(12) United States Patent
Meyer

(10) Patent No.: US 7,263,282 B2
(45) Date of Patent: Aug. 28, 2007

(54) ELECTRICALLY HEATED VAPOUR DISPENSING APPARATUS

(75) Inventor: Brian Robert Meyer, Mowbray (GB)

(73) Assignee: Reckitt Benckiser (UK) Limited, Slough, Berkshire (GB)

( * ) Notice: Subject to any disclaimer, the term of this patent is extended or adjusted under 35 U.S.C. 154(b) by 0 days.

(21) Appl. No.: 10/519,777

(22) PCT Filed: Jul. 1, 2003

(86) PCT No.: PCT/GB03/02801

§ 371 (c)(1),
(2), (4) Date: Dec. 29, 2004

(87) PCT Pub. No.: WO2004/002542

PCT Pub. Date: Jan. 8, 2004

(65) Prior Publication Data

US 2005/0155985 A1    Jul. 21, 2005

(30) Foreign Application Priority Data

Jul. 1, 2002    (GB) ................. 0215145.4

(51) Int. Cl.
*A61H 33/06*    (2006.01)
(52) U.S. Cl. ...................... 392/394; 392/386
(58) Field of Classification Search ..................... None
See application file for complete search history.

(56) References Cited

U.S. PATENT DOCUMENTS 4,977,309 A    12/1990    Uchida ................. 219/541
5,574,821 A    11/1996    Babasade ................. 392/392
5,644,866 A    7/1997    Katsuda et al. ............... 43/129
6,909,840 B2 *    6/2005    Harwig et al. .............. 392/405

FOREIGN PATENT DOCUMENTS

| GB | 2 117 639 | 10/1983 |
| GB | 2 347 860 A | 9/2000 |
| GB | 2 357 973 A | 7/2001 |
| WO | WO98 46283 A | 10/1998 |
| WO | WO 01 39809 A | 6/2001 |

OTHER PUBLICATIONS

International Search Report dated Sep. 16, 2003 for Application No. PCT/GB03/02801.
International Preliminary Examination Report dated Nov. 10, 2004 for Application No. PCT/GB03/02801.

* cited by examiner

*Primary Examiner*—Thor S Campbell
(74) *Attorney, Agent, or Firm*—Norris McLaughlin & Marcus, PA

(57) ABSTRACT

An electrically heated apparatus for dispensing fragrancing materials and other volatile substances to an enclosed volume comprising a container containing a quantity of a volatile substance, heating means, transfer means for transferring said volatile substance towards said heating means and a portable power supply for energizing said heating means, characterized in that said heating means comprises a flexible thin film heater.

28 Claims, 2 Drawing Sheets

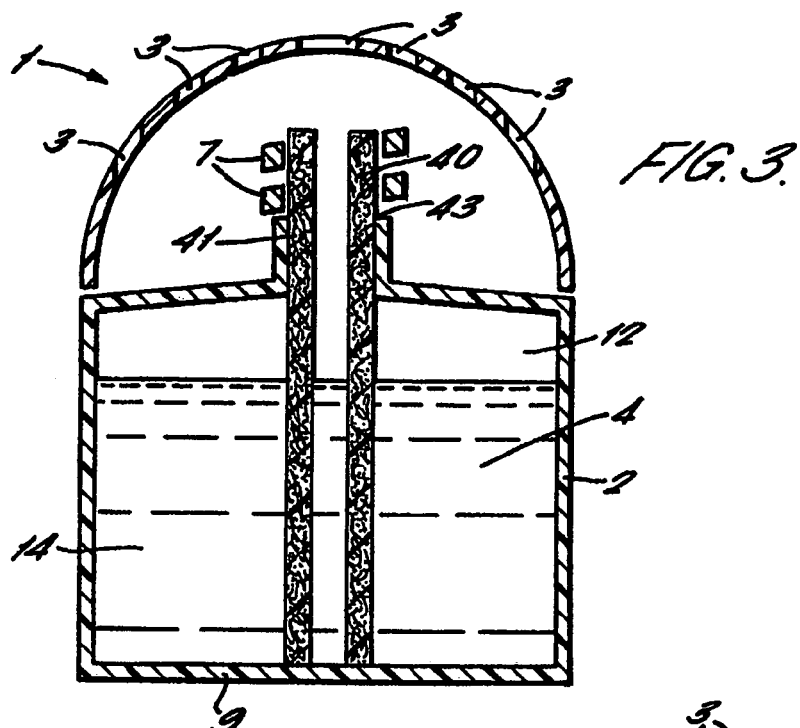
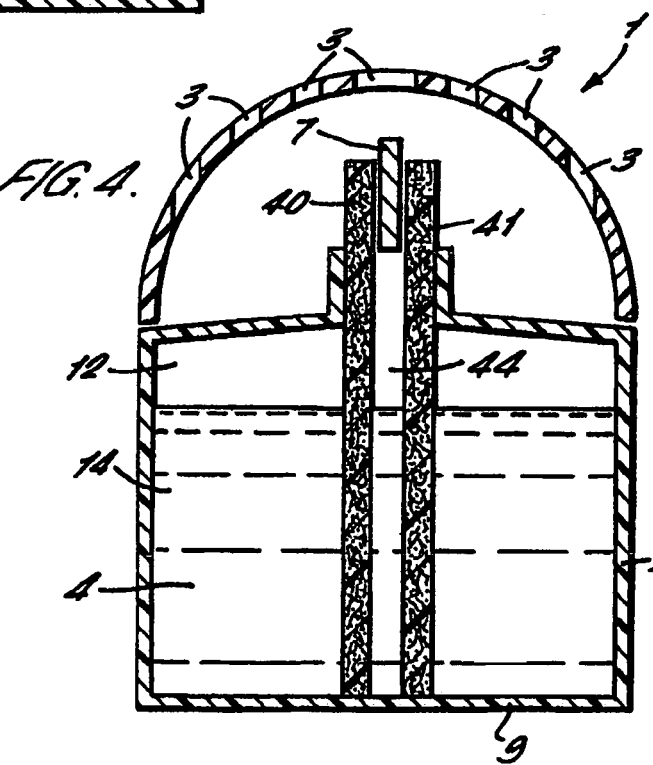
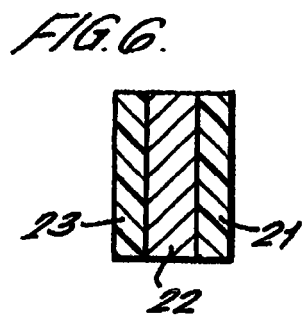
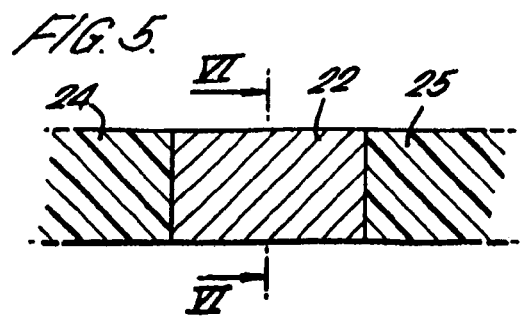

ELECTRICALLY HEATED VAPOUR DISPENSING APPARATUS

The present invention relates to an electrically heated vapour dispensing apparatus of the type commonly used for dispensing fragrancing materials and other volatile substances to an enclosed volume such as the interior of a room.

Electrically heated vapour dispensing apparatus of different types are known in the art. For example, GB 2 117 639 describes an air freshening device of the type which is plugged into an electrical mains socket. Whilst such "plug-in" apparatus provide a satisfactory volatilisation of fragrance, they have a number of disadvantages. Firstly, the devices must be plugged into an electrical socket in order to operate. Consequently, the electrical socket is unavailable for other uses. Secondly, the heating elements used in the apparatus need to operate continuously otherwise there is a performance drop. Consequently, the apparatus uses a large amount of electrical energy. In addition a user is prone to become 'habituated' to the fragrance—a phenomenon whereby exposure to a continuous presence of a fragrance leads one to become desensitised to the fragrance with the result that one can no longer detect the presence of the fragrance. Thirdly, such apparatus cannot be used where electrical mains sockets are not available, for example, in bathrooms, out-houses, etc. Fourthly, the majority of electrical mains sockets are located at or near ground level where the socket may be difficult to access or is obscured by items such as furniture. Locating the apparatus at or near ground level is not always considered ideal from an aesthetic consideration or for maximising the efficient volatilisation and diffusion of the fragrance in the enclosed volume of the room.

Attempts have been made to provide an electrically heated vapour dispensing apparatus which operates from a portable power supply, such as batteries. However, such apparatus suffer from two main drawbacks. Firstly, they are under-powered such that they have difficulty in heating the fragrance or other volatile substance to the required temperature, as well as heating the volatile substance sufficiently rapidly. Secondly, batteries are not able to volatilise the fragrance for a long enough period to be acceptable to consumers. With many conventional apparatus the operating life of a battery power source would be only a matter of hours.

According to the present invention, there is provided an electrically heated apparatus for dispensing fragrancing materials and other volatile substances to an enclosed volume comprising a container containing a quantity of a volatile substance, heating means, transfer means for transferring said volatile substance towards said heating means and a portable power supply for energising said heating means, characterised in that said heating means comprises a flexible thin film heater comprising a laminate having at least one laminar of resistive material and two insulating laminars attached to opposed surfaces of the resistive material laminar. Other aspects of the present invention are defined in the attached claims.

Embodiments of the present invention will now be described, by way of example only, with reference to the accompanying drawings in which:

FIG. 3 is a schematic cross-sectional view through a third embodiment of electrically heated vapour dispensing apparatus according to the present invention;

FIG. 4 is a schematic cross-sectional view through a fourth embodiment of electrically heated vapour dispensing apparatus according to the present invention;

FIG. 5 is a plan view of a heating means for use, in the apparatus of FIGS. 1 to 4; and FIG. 6 is a cross-sectional view of the heating means taken on line VI-VI of FIG. 5.

Figure 1:
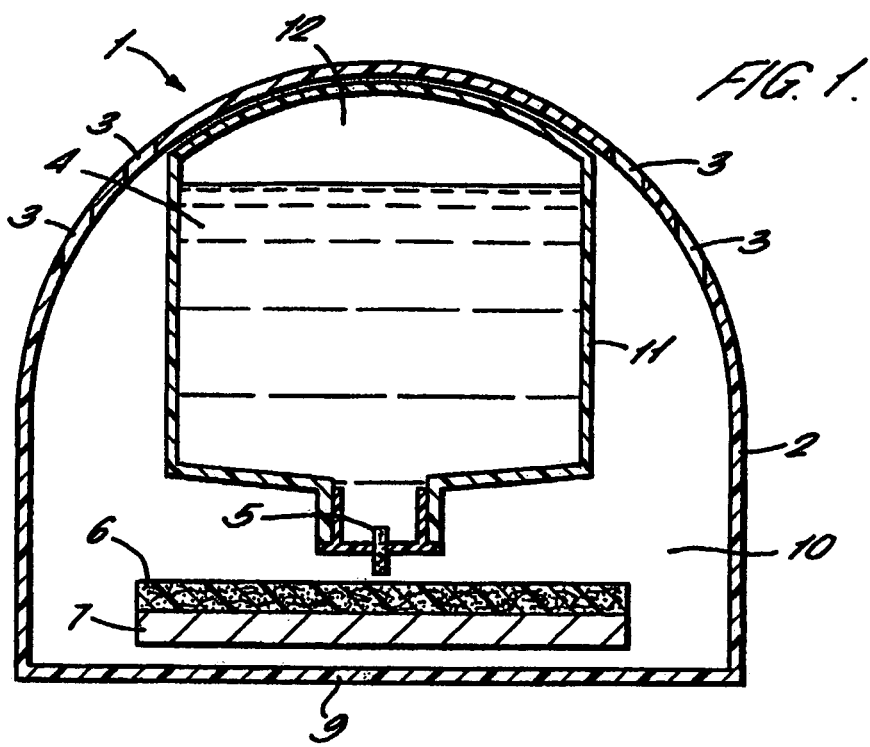
FIG. 1 is a schematic cross-sectional view through a first embodiment of electrically heated vapour dispensing apparatus according to the present invention.

FIG. 1 shows a first embodiment of electrically heated vapour dispensing apparatus 1 which comprises a housing 2 containing a fragrance reservoir 4, a capillary tube 5, a porous element 6, heating means 7, control circuitry (not shown) and a portable power supply (not shown).

The housing 2 has a planar base 9 allowing the apparatus 1 to be stood upright on a flat surface. The housing 2 defines an interior 10 of the apparatus 1 in which the other components of the apparatus 1 are located. At or near an upper end of the housing 2 are provided a number of air holes 3 providing communication between the interior 10 and the surrounding atmosphere. The air holes 3 allow volatilised fragrance to emanate from the interior 10.

The housing 2 may be formed from a thermoplastic or thermosetting polymeric material which has sufficient heat tolerance such that it is not undesirably softened or melted when the heating means 7 is energised during normal use of the apparatus 1. Typical examples of known materials which would be suitable include polymers and/or co-polymer resin compositions based on: nylons, polyethylene terephthalate, polybutylene terephthalate, polyolefins, styrenes, polyacetal resins, polysulfones as well as other materials which exhibit the desired heat tolerance properties as noted above. As is well-known in the art, the polymeric compositions may include additives or modifiers such as fillers, fire retardant materials, colourants, pigments, etc. Preferably, the housing is formed in an injection moulding process. Further, the housing 2 may be formed from glass.

The fragrance reservoir 4 is mounted in the interior 10 of the apparatus 1 and comprises a reservoir body 11 defining a closed volume 12 in which is stored a volume of the fragrance 14 to be volatilised. The fragrance 14 is typically a volatile liquid composition.

A lower end of the reservoir body 11 narrows to form a neck portion 13 in which is located the capillary tube 5. The capillary tube 5 provides the sole outlet for the fragrance 14 to exit the reservoir 4.

The porous element 6 is located immediately below and in contact with the outlet of the capillary tube 5. The porous element 6 may take various forms and shapes. The porous element 6 may be a porous polymeric material such as a sintered polymeric material or a porous ceramic material. Suitable materials include the range of porous plastics produced by Porex® (Fairbairn, Ga., U.S.A.). Alternatively, the porous element 6 may be a fibrous material such as a block, pad or sponge of compressed, woven or non-woven fibrous material. Exemplary fibrous materials include naturally occurring synthetic fibrous materials as well as blends of two or more such fibrous materials.

The heating means 7 is located underneath the porous element 6 and in register therewith. In accordance with the present invention, the heating means 7 is a flexible, thin film heater. The thin film heater 7 is attached to the lower surface of the porous element 6 or otherwise held in contact therewith such that the porous element 6 is interposed between the capillary tube 5 and thin film heater 7.

As shown in FIGS. 5 and 6, the thin film heater comprises a laminate of three layers: an upper layer 21 of insulating material, a lower layer 23 of insulating material and an intermediate layer 22 of resistive material. The intermediate layer 22 of resistive material may be formed from a PTF material (polymer thick film) which preferably has PTC characteristics (positive co-efficient temperature) such that as the temperature of the resistive material 22 increases, the electrical resistance of the material also increases thus limiting the danger of over-currents and damage to the resistive material 22 and surrounding apparatus 1. The resistive material 22 is provided with contact portions 24 and 25 of conductive material to allow the resistive material 22 to be connected as part of an electrical circuit.

The resistive material 22 of the thin film heater 7 may be formed from a resistive ink or a resistive wire or a combination of the two. Resistive ink films are available from Hydor. Resistive wire films are available from Mintco. The ink and/or wire is laid down in thin layers of the order of 40 to 50 microns on the flexible substrate of the insulating layers 21 and 23.

Advantageously, the resistive material 22 displays a very rapid thermal response on energisation. The time required for the resistive material 22 to reach an operating temperature of approximately 70 degrees Celsius is in the order of one to two seconds. In addition the cooling time of the film is equally rapid. Consequently, the thin film heater 7 is able to deliver a precise quantity of heat energy to the porous element 6 which allows for precise volatilisation of the fragrance 14. The operating temperature of the heater 7 can be adjusted depending on the nature and characteristics of the substance to be volatilised. For fragrances, typical temperatures are in the range 40 to 90 degrees Celsius, more preferably, 60 to 80 degrees Celsius. For other substances such as insecticides higher temperatures may be required: in the range 100 to 160 degrees Celsius, more preferably 120 to 140 degrees Celsius, typically 130 degrees Celsius.

An important advantage of using a thin film heater as described above is that the heater may be formed as a flexible element and does not require a rigid substrate. Consequently, the thin film heater 7 may be manipulated to fit into a small volume and/or be positioned to accommodate other components within the interior 10 of the apparatus 1. As such, the use of a thin film flexible heater allows for a smaller overall volume of apparatus 1. The use of a flexible heater also allows the spatial relationship of the heater 7 and porous element 6 or other fragrance-bearing element to be easily adjusted in order to maximise thermal efficiency as described below in subsequent embodiments.

The portable power supply preferably comprises a battery cell or cells. The batteries may, for example, be of the alkaline, lithium-ion or Ni-Cad type. The batteries may be disposable or rechargeable. The batteries may be rechargeable in situ by, for example, a solar cell or may be removable from the housing 2 to allow recharging by connection to a mains electrical supply.

Control circuitry is provided in housing 2. The control circuit includes a switch and a timer. The switch operates to open and close an electric circuit comprising the portable power supply and thin film heater 7 and hence controls flow of electric current around the electrical circuit. Consequently, the switch controls energisation of the heater 7 and fragrance volatilisation. The switch is operated by the timer. The timer can be pre-programmed to open and close the switch at specified times or to open and close the switch for set periods and at set intervals. For example, the apparatus 1 can be switched on for periods ranging between one second and five minutes or more. Preferably, each period is between one second and one minute. Alternatively, each period is between one second and ten seconds. Alternatively, each period is between one second and five seconds.

Alternatively the timer may be programmed on demand by the user. For example, a selector switch may be provided to allow the user to adjust the period of energisation or the interval length between energisations. The switch may also be opened and held opened by the user manually so as to place the apparatus 1 in an 'off' state. Alternatively a secondary, 'master', switch may be provided for this purpose.

An important advantage of using a switch and timer is that the overall power requirement of the apparatus is reduced. This in turn allows the useful life of the apparatus 1 to be extended by increasing the length of time for which the apparatus 1 can operate between battery replacement or recharge. An added advantage is that habituation to the fragrance is reduced since the fragrance is volatilised only for discrete periods and not continuously.

In use, a user switches the apparatus 1 on using the switch or master switch. Fragrance 14 from the reservoir 4 is drawn by capillary action down capillary tube 5 where it contacts and impregnates the porous element 6. The control circuit passes electric current from the battery to the thin film heater 7 as and when the timer operates the switch to close the electric circuit. On energisation, the thin film heater 7 rapidly heats up to its operating temperature. Heat energy is passed from the thin film heater 7 to the porous element 6 by conduction. Consequently, the porous element 6 heats up leading to volatilisation of fragrance 14 impregnated therein. The volatilised particles of fragrance then emanate though the air holes 3 into the surrounding atmosphere. Once the programmed energisation period has expired the control circuitry opens the switch turning the heater 7 off. The thin film heater 7 rapidly cools leading to rapid cessation of fragrance emanation.

Figure 2:
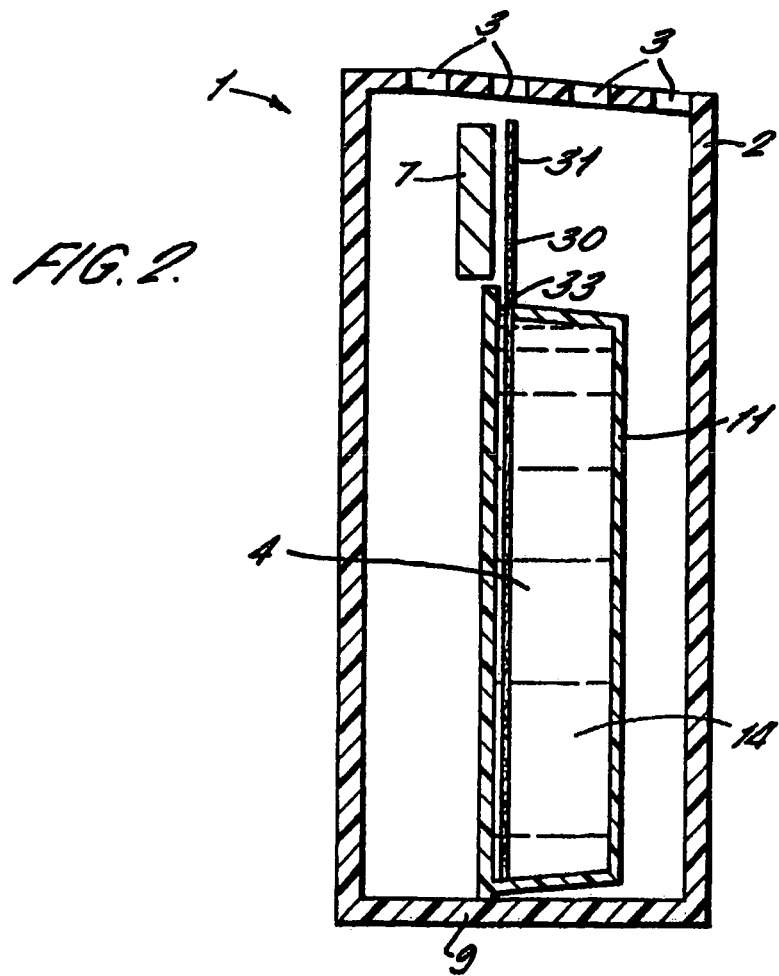
FIG. 2 is a schematic cross-sectional view through a second embodiment of electrically heated vapour dispensing apparatus according to the present invention.

FIG. 2 shows a second embodiment of apparatus 1 according to the present invention. As before, the apparatus 1 comprises a housing 2 having air holes 3, a fragrance reservoir 4, control circuitry (not shown), portable power supply (not shown) and a thin film heater 7. The second embodiment is distinguished from the first embodiment by the means of delivering the fragrance 14 into the vicinity of the thin film heater 7. A wick 30 is provided which extends externally from within the interior 12 of the fragrance reservoir 4. An upper end 31 of the wick 30 passes through an aperture 33 in the reservoir body 11 and extends therefrom. The thin film heater 7 is attached of held in contact with the upper end 31 of the wick 30. A capillary film may be used in substitution for the wick 30.

In use, operation of the portable power supply, control circuitry and thin film heater 7 is as described above with reference to the first embodiment. Fragrance 14 is wicked upwardly from within the reservoir 4 towards the upper end 31 of the wick 30. Energisation of the thin film heater 7 causes volatilisation of the fragrance which is then emanated though the air holes 3.

Advantageously, no capillary tube is required.

FIG. 3 shows a third embodiment of apparatus 1 according to the present invention. As before, the apparatus 1 comprises a housing 2 having air holes 3, a fragrance reservoir 4, control circuitry (not shown), portable power supply (not shown) and a thin film heater 7. The third embodiment is distinguished from the previous embodiments by the means of delivering the fragrance 14 into the vicinity of the thin film heater 7. A wick 40 is provided which extends externally from within the interior 12 of the fragrance reservoir 4. An upper end 41 of the wick 40 passes through an aperture 43 in the reservoir body 11 and extends therefrom. The wick 40 is cylindrical in shape and hollow. The wick 40 is preferably formed from a porous polymeric material or fibrous material. Suitable types of materials include those described above with reference to the porous element 6 of the first embodiment. The thin film heater 7 is attached of held in contact with the upper end 41 of the wick 40. Advantageously, the thin film heater 7 is formed as an elongate strip which is wrapped around an external surface of the cylindrical wick 40 in a spiral arrangement. This serves to maximise the surface area of the wick 40 in proximity to the thin film heater 7 whilst minimising the quantity of resistive material 22 in the heater 7 and hence minimise the power requirements of the apparatus 1.

Operation of the third embodiment is the same as that of the embodiments described above.

FIG. 4 shows a fourth embodiment of apparatus 1 according to the present invention. The fourth embodiment is similar to the third embodiment and in particular the wick 40 is in the form of a hollow cylindrical wick. The thin film heater 7 is inserted into a bore 44 of the wick 40 such that the heater 7 is surrounded by wick material. Advantageously heat generated by the heater 7 is efficiently conducted to the wick 40 due to the wick 40 forming a barrier such that the heat energy cannot easily emanate other than by conduction through the wick 40.

Whilst in the foregoing description the apparatus 1 has been described for use in volatising fragrance, it is to be understood that the apparatus is equally suitable for the volatilisation of other volatile substances which are desired to be emanated including, but not limited to, perfumes, disinfecting compositions and insecticides.

Whilst in the foregoing description the fragrance 14 has been typified as a liquid composition, other compositions may be utilised. These include gels, pastes and thixotropic liquids, as well as combinations of the same. The fragrance 14 may further comprise a liquid composition adsorbed onto a carrier element such as silica. The fragrance 14 may, in addition, be a bi-phase or multi-phase fragrance.

Whilst in the foregoing description the apparatus 1 has been described as for use with compositions such as fragrances, the apparatus may also be readily used in medical application for dispensing, for example, metered dosing of compounds such as aromatherapy compositions.

Whilst in the foregoing description the control circuitry has been described as switching the thin film heater 7 from an off state to an energised state the control circuitry can also be programmed to switch the thin film heater 7 from a 'low power' state to a 'high power' state. Thus constant emanation of the volatile substance is achieved with the heater 7 in the low power setting whilst fragrance emanation is boosted at set intervals when the heater 7 is switched to the high power setting. This embodiment is advantageous where a strong fragrance presence is required.

The invention claimed is:

1. An electrically heated apparatus for dispensing fragrancing materials or other volatile substances to an enclosed volume comprising
    a heating means consisting of a flexible film heater having at least one layer of resistive material which is from a resistive ink, a resistive wire or a combination thereof, two insulating layers attached to opposed surfaces of the layer of the resistive material, and contact portions of conductive material in electrical contact with resistive material;
    a container containing a quantity of a volatile substance;
    a transfer means for transferring said volatile substance towards said heating means, wherein said transfer means comprises a cylindrical wick and said heating means is located in a bore of the cylindrical wick; and
    a portable power supply for energising said heating means.

2. Electrically heated apparatus according to claim 1 wherein the resistive material has positive temperature coefficient characteristics.

3. Electrically heated apparatus according to claim 1 wherein the layer of resistive material of the flexible film heater is formed from one or more layers of resistive ink or resistive wire, each layer having a thickness of between 10 and 1000 microns.

4. Electrically heated apparatus according to claim 3 wherein the layer of resistive material is formed from one or more layers of resistive ink or resistive wire each layer having a thickness of between 10 and 100 microns.

5. Electrically heated apparatus according to claim 4 wherein the layer of resistive material is formed from one or more layers of resistive ink or resistive wire, each layer having a thickness of between 20 and 50 microns.

6. Electrically heated apparatus according to claim 1 wherein the flexible film heater has an overall thickness of between 20 and 1000 microns.

7. Electrically heated apparatus according to claim 6 wherein the flexible film heater has an overall thickness of between 40 and 100 microns.

8. Electrically heated apparatus according to claim 1 wherein the portable power supply comprises one or more battery cells.

9. Electrically heated apparatus according to claim 8 wherein the battery cell or cells are rechargeable.

10. Electrically heated apparatus according to claim 1 wherein said transfer means comprises a capillary tube.

11. The electrically heated apparatus according to claim 1, wherein the heating means is characterized in being heatable to a temperature between 40 and 90 degrees Celsius.

12. Electrically heated apparatus according to claim 1 further comprising timing means operable to energise said heating means periodically.

13. Electrically heated apparatus according to claim 12 wherein the periodicity is pre-programmed.

14. Electrically heated apparatus according to claim 12 wherein the periodicity is user defined.

15. Electrically heated apparatus according to claim 12 wherein each period of energisation is for between 1 second and 5 minutes.

16. Electrically heated apparatus according to claim 12 wherein each period of energisation is for between 1 second and 1 minute.

17. Electrically heated apparatus according to claim 1 further comprising timing means operable to switch said heating means periodically from a low power state to a high power state.

18. Electrically heated apparatus according to claim 1, wherein the heating means is characterized in being heatable to a temperature between 40 and 90 degrees Celsius.

19. Electrically heated apparatus according to claim 18, wherein the heating means is characterized in being heatable to a temperature between 40 and 80 degrees Celsius.

20. An electrically heated apparatus for dispensing fragrancing materials or other volatile substances to an enclosed volume comprising
    a heating means consisting of a flexible film heater having at least one layer of resistive material which is formed from a resistive ink, a resistive wire or a combination thereof, two insulating layers attached to opposed surfaces of the layer of the resistive material, and contact portions of conductive material in electrical contact with resistive material;

a container containing a quantity of a volatile substance;

a transfer means for transferring said volatile substance towards said heating means, wherein the transfer means is a cylindrical wick, and the heating means is formed as an elongate strip which is wrapped around an external surface of said cylindrical wick in a spiral arrangement; and a portable power supply for energizing said heating means.

21. Electrically heated apparatus according to claim 1, wherein the resistive material of the flexible film heater, when electrically energized, reaches from an ambient temperature an operating temperature of approximately 70 degrees Celsius in not more than 2 seconds.

22. The electrically heated apparatus according to claim 20 wherein the resistive material has positive temperature coefficient characteristics.

23. The electrically heated apparatus according to claim 20 wherein the layer of resistive material of the flexible film heater is formed from one or more layers of resistive ink or resistive wire, each layer having a thickness of between 10 and 1000 microns.

24. The electrically heated apparatus according to claim 20 wherein the flexible film heater has an overall thickness of between 20 and 1000 microns.

25. The electrically heated apparatus according to claim 20 wherein the portable power supply comprises one or more battery cells.

26. The electrically heated apparatus according to claim 20 further comprising timing means operable to energize said heating means periodically.

27. The electrically heated apparatus according to claim 20 further comprising timing means operable to switch said heating means periodically from a low power state to a high power state.

28. The electrically heated apparatus according to claim 20, wherein the resistive material of the flexible film heater, when electrically energized, reaches from an ambient temperature an operating temperature of approximately 70 degrees Celsius in not more than 2 seconds.

* * * * *